United States Patent
Chen et al.

(10) Patent No.: US 8,163,907 B2
(45) Date of Patent: Apr. 24, 2012

(54) DIHYDROPYRIDINE CALCIUM ANTAGONIST COMPOUNDS, PREPARATION METHODS, AND MEDICAL USES THEREOF

(75) Inventors: Guo-hua Chen, Fujian (CN); Li Wang, Fujian (CN)

(73) Assignee: Cosunter Pharmaceutical Company, Fujian (CN)

( * ) Notice: Subject to any disclaimer, the term of this patent is extended or adjusted under 35 U.S.C. 154(b) by 0 days.

(21) Appl. No.: 12/863,593

(22) PCT Filed: Jan. 5, 2009

(86) PCT No.: PCT/CN2009/070031
§ 371 (c)(1),
(2), (4) Date: Jul. 20, 2010

(87) PCT Pub. No.: WO2009/092301
PCT Pub. Date: Jul. 30, 2009

(65) Prior Publication Data
US 2011/0201811 A1   Aug. 18, 2011

(30) Foreign Application Priority Data
Jan. 21, 2008   (CN) .......................... 2008 1 0018711

(51) Int. Cl.
*C07D 401/12*   (2006.01)
*C07D 213/80*   (2006.01)
(52) U.S. Cl. ....................................... 544/365; 546/321
(58) Field of Classification Search .................. None
See application file for complete search history.

(56) References Cited

OTHER PUBLICATIONS

CardiovascularDisease, http://en.wikipedia.org/wiki/Cardiovascular_disease (2011).*
Artherosclerosis, http://journals.lww.com/jhypertension/Abstract/1993/03001/Anti_atherosclerotic_effects_of_calcium.10.aspx (2011).*
Meguro et al., caplus an 1986:533842.*

* cited by examiner

*Primary Examiner* — Sun Jae Loewe

(57) ABSTRACT

A dihydropyridine (DHP) calcium antagonist compound and its preparation method and medical use are related to preparation methods of compounds of general formulas (I) and (II) as shown below and their pharmaceutical salts and applications for treating cardiovascular diseases, and $R_1$ represents a substituted or unsubstituted heterocyclic, aromatic ring or aralkyl group, and the substituent may be $C_1$-$C_4$ alkyl, $C_1$-$C_4$ alkoxyl, halogen, cyano, trifluoromethyl, trifluoromethoxyl, methylthio, nitro, amino or hydroxyl group; $R_2$ represents a $C_1$-$C_8$ alkyl group; $R_3$ and $R_4$ are the same or different, and each represents a hydrogen, halogen, cyano, trifluoromethyl, trifluoromethoxyl, methylthio, nitro or amino group or a $C_1$-$C_4$ alkyl, $C_1$-$C_4$ alkoxyl, $C_1$-$C_4$ alkenyl, or $C_1$-$C_4$ alkinyl group; $R_5$ and $R_6$ are the same or different, and each represents a $C_1$-$C_4$ alkyl group; X represents O, S or a single bond; m=0-6, n=1-6, and m and n are the same or different.

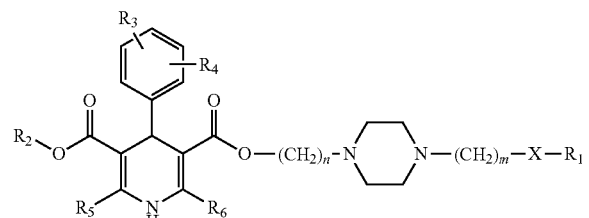

(I)

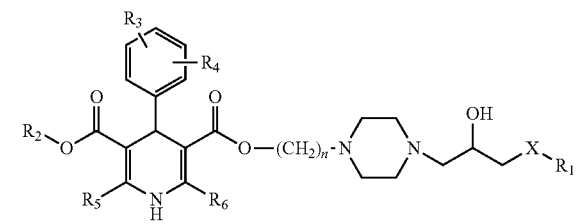

(II)

9 Claims, No Drawings

DIHYDROPYRIDINE CALCIUM ANTAGONIST COMPOUNDS, PREPARATION METHODS, AND MEDICAL USES THEREOF

BACKGROUND OF THE INVENTION

1. Field of the Invention

The present invention relates to dihydropyridine (DHP) calcium antagonist compounds, and more particularly to DHP calcium antagonist compounds, preparation methods, and medical applications for the treatment of cardiovascular diseases.

2. Description of the Related Art

Calcium antagonist, also known as calcium channel blocker, can be used for suppressing calcium influx across membranes and calcium release in cells, reducing the calcium ion concentration in the cells and the utility rate of calcium ions, suppressing the activity of adenosine triphosphatase (ATPase) activity, reducing cardiomuscular contraction force, relaxing smooth muscle cells dilating blood vessels, and lowering the resistance of peripheral blood vessels. Clinically, calcium antagonist is mainly used for the treatment of hypertension, angina, arrhythmia, dilated cardiomyopathy and ischemic heart disease, etc., and extensively used as a cardiovascular medicine. As increasingly more new medicines are introduced to the market, the DHP particularly catches our attention, since the DHP not only provides an excellent medical effect for lowering blood pressures, but also has little side effects, and a low price. The DHP has become a first-tier clinical medicine.

As the first DHP calcium antagonist nifedipine (1) launched to the market, its side-chain ester structure is electrically neutral, and thus having poor water solubility and absorption; and an amino side chain with a good water solubility is introduced to the nicardipine (2) ester group to give a better absorption effect, but it does not provide a long-lasting calcium antagonistic effect due to the first pass effect of the liver or the quick metabolism of the body. When we are looking for a new DHP medicine, a piperazine group using an aromatic branched chain is provided to substitute an amino structure of a side chain of an ester group in the structure of a substituted nicardipine medicine. With the fat solubility of the aromatic branched chain and the space hindrance of large substituent groups, the combination of medicines and receptors is affected to change the chemical properties of medicines and delay metabolism. According to this hypothesis, a series of DHP compounds with piperazine esters are synthesized.

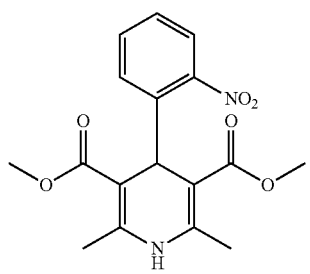

1

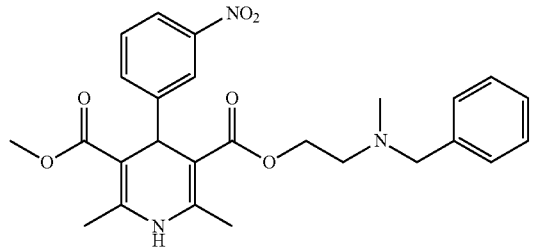

2

SUMMARY OF THE INVENTION

In view of the drawbacks of the prior art, the present invention intends to overcome the following technical issues: finding a way of how to apply the fundamental theory of medicine design and integrating the computer-aided drug design to synthesize a series of new DHP compounds having a better activity of calcium antagonisis and screen the activity of resistant hypertension, in hope of obtaining new resistant hypertension drugs having a resistant hypertension activity better than those of the existing medicines for treating hypertension diseases.

Another objective of the present invention is to provide a preparation method of the aforementioned compounds.

A further objective of the present invention is to apply these compounds for treating cardiovascular diseases.

To achieve the aforementioned objectives, the present invention provides the following technical solutions:

Compounds or their pharmaceutical salts of general formula (I):

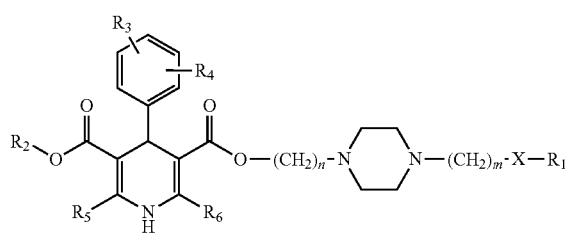

(I)

where, $R_1$ represents a substituted or unsubstituted heterocyclic, aromatic ring or aralkyl group, and the substituent can be a $C_1$-$C_4$ alkyl group, a $C_1$-$C_4$ alkoxyl group, a halogen, a cyano group, a trifluoromethyl group, a trifluoromethoxyl group, a methylthio group, a nitro group, an amino group or a hydroxyl group.

$R_2$ represents a $C_1$-$C_8$ alkyl group, and the alkyl group selectively has a hydroxyl group or a $C_1$-$C_6$ alkoxyl substituent.

$R_3$ and $R_4$ can be the same or different, and each represents hydrogen, a halogen, a cyano-group, a trifluoromethyl group, a trifluoromethoxyl group, a methylthio group, a nitro group, amino group or a $C_1$-$C_4$ alkyl group, a $C_1$-$C_4$ alkoxyl group, a $C_1$-$C_4$ alkenyl group, or a $C_1$-$C_4$ alkinyl group.

$R_5$ and $R_6$ can be same or different, and each represents a $C_1$-$C_4$ alkyl group, and the alkyl group selectively has a hydroxyl group or a $C_1$-$C_4$ alkoxyl substituent.

X represents O, S or a single bond.

m=0-6, n=1-6, and m and n are the same or different.

Compounds or their pharmaceutical salts of general formula (II):

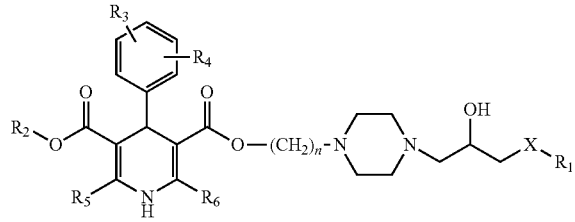

where, $R_1, R_2, R_3, R_4, R_5, R_6, X$, and n are defined the same as above.

In the present invention, $R_1$ is preferably 2-methooxyphenyl, 2,3-dichlorophenyl group, p-nitrophenyl group, p-methylphenyl group, methyl diphenyl group; $R_2$ is preferably methyl group and ethyl group; $R_3$ is preferably hydrogen; $R_4$ is preferably 3-nitro group; $R_5$ and $R_6$ are preferably a methyl group, X is preferably O or a single bond; m is preferably equal to 0, 1, 2, 3; and n is preferably equal to 2, 3, 4.

In the present invention, the pharmaceutical salts include salts of compounds of general formulas (I) and (II) and salts formed by the following acids: sulfuric acid, nitric acid, hydrochloric acid, hydrobromic acid, phosphoric acid, formic acid, acetic acid, maleic acid, citric acid, tartaric acid, lactic acid, benzenesulfonic acid, p-methylbenzenesulfonic acid, pyruvic acid, or furamic acid. The preferred pharmaceutical salts are monohydrochloride salts or dihydrochloride salts of compounds of general formulas (I) and (II).

Preferred compounds of general formulas (I) and (II) or their pharmaceutical salts include:

1,4-dihydro-2,6-dimethyl-4-(3-nitrophenyl)-3,5-pyridinecarboxylic acid methyl ester2-(N-4-(3-(2-methoxyphenoxy)propyl)piperazinyl)ethyl ester ($I_1$), 1,4-dihydro-2,6-dimethyl-4-(3-nitrophenyl)-3,5-pyridinecarboxylic acid methyl ester3-(N-4-(3-(2-methoxyphenoxy)propyl)piperazinyl)propyl ester ($I_2$);

1,4-dihydro-2,6-dimethyl-4-(3-nitrophenyl)-3,5-pyridinecarboxylic acid methyl ester-4-(N-4-(3-(2-methoxyphenoxy)propyl)piperazinyl)butyl ester ($I_3$), 1,4-dihydro-2,6-dimethyl-4-(3-nitrophenyl)-3,5-pyridinecarboxylic acid methyl ester3-(N-4-(2-(2-methoxyphenoxy)ethyl)piperazinyl)propyl ester hydrochloride ($I_4$);

1,4-dihydro-2,6-dimethyl-4-(3-nitrophenyl)-3,5-pyridinecarboxylic acid methyl ester-4-(N-4-(2-(2-methoxyphenoxy)ethyl)piperazinyl)butyl ester hydrochloride ($I_5$), 1,4-dihydro-2,6-dimethyl-4-(3-nitrophenyl)-3,5-pyridinecarboxylic acid methyl ester2-(N-4-(diphenylmethoxy ethyl)piperazinyl)ethyl ester hydrochloride (I6);

1,4-dihydro-2,6-dimethyl-4-(3-nitrophenyl)-3,5-pyridinecarboxylic acid methyl ester3-(N-4-(diphenylmethoxy ethyl)piperazinyl)propyl ester hydrochloride ($I_7$), 1,4-dihydro-2,6-dimethyl-4-(3-nitrophenyl)-3,5-pyridinecarboxylic acid methyl ester2-(N-4-(4-nitrobenzl)piperazinyl)ethyl ester hydrochloride ($I_8$), 1,4-dihydro-2,6-dimethyl-4-(3-nitrophenyl)-3,5-pyridinecarboxylic acid methyl ester3-(N-4-(4-nitrobenzl)piperazinyl)propyl ester hydrochloride ($I_9$), 1,4-dihydro-2,6-dimethyl-4-(3-nitrophenyl)-3,5-pyridinecarboxylic acid methyl ester3-(N-4-(4-methylbenzl)piperazinyl)propyl ester hydrochloride ($I_{10}$), 1,4-dihydro-2,6-dimethyl-4-(3-nitrophenyl)-3,5-pyridinecarboxylic acid methyl ester2-(N-4-(2,3-dichlorophenyl) piperazinyl)ethyl ester ($I_{11}$);

1,4-dihydro-2,6-dimethyl-4-(3-nitrophenyl)-3,5-pyridinecarboxylic acid methyl ester3-(N-4-(2,3-dichlorophenyl) piperazinyl)propyl ester hydrochloride ($I_{12}$);

1,4-dihydro-2,6-dimethyl-4-(3-nitrophenyl)-3,5-pyridinecarboxylic acid methyl ester-4-(N-4-(2,3-dichlorophenyl)piperazinyl)butyl ester hydrochloride ($I_{13}$);

1,4-dihydro-2,6-dimethyl-4-(3-nitrophenyl)-3,5-pyridinecarboxylic acid methyl ester2-(N-4-(2-(2-methoxyphenoxy)ethyl)piperazinyl)ethyl ester hydrochloride ($I_{14}$);

1,4-dihydro-2,6-dimethyl-4-(3-nitrophenyl)-3,5-pyridine carboxylic acid ethyl ester 2-(N-4-(2-(2-methoxyphenoxy)ethyl)piperazinyl)ethyl ester ($I_{15}$);

1,4-dihydro-2,6-dimethyl-4-(3-nitrophenyl)-3,5-pyridine carboxylic acid ethyl ester3-(N-4-(2-(2-methoxyphenoxy) ethyl)piperazinyl)propyl ester ($I_{16}$);

1,4-dihydro-2,6-dimethyl-4-(3-nitrophenyl)-3,5-pyridine carboxylic acid ethyl ester 2-(N-4-(3-(2-methoxyphenoxy)propyl)piperazinyl)ethyl ester ($I_{17}$);

1,4-dihydro-2,6-dimethyl-4-(3-nitrophenyl)-3,5-pyridine carboxylic acid ethyl ester 3-(N-4-(3-(2-methoxyphenoxy)propyl)piperazinyl)propyl ester ($I_{18}$);

1,4-dihydro-2,6-dimethyl-4-(3-nitrophenyl)-3,5-pyridinecarboxylic acid methyl ester2-(N-4-(3-(2-methoxyphenoxy)-2-hydroxpropyl)piperazinyl)ethyl ester hydrochloride ($II_1$);

1,4-dihydro-2,6-dimethyl-4-(3-nitrophenyl)-3,5-pyridinecarboxylic acid methyl ester3-(N-4-(3-(2-methoxyphenoxy)-2-hydroxpropyl)piperazinyl)propyl ester hydrochloride ($II_2$), 1,4-dihydro-2,6-dimethyl-4-(3-nitrophenyl)-3,5-pyridinecarboxylic acid methyl ester4-(N-4-(3-(2-methoxyphenoxy)-2-hydroxpropyl)piperazinyl) butyl ester hydrochloride ($II_3$)

A preparation method of compounds of general formula (I) comprises the steps of having a substitution reaction between compounds of general formulas Ib and Ic or between the compounds of general formulas Ia and Id.

More specifically, a compound of general formula Ib has a substitution reaction with a compound of general formula Ic under the catalysis of NaOH; or a compound of general formula Ib has a substitution reaction with a compound of general formula Ic under the catalysis of triethylamine; or a compound of general formula Ib has a substitution reaction with a compound of general formula Ic directly.

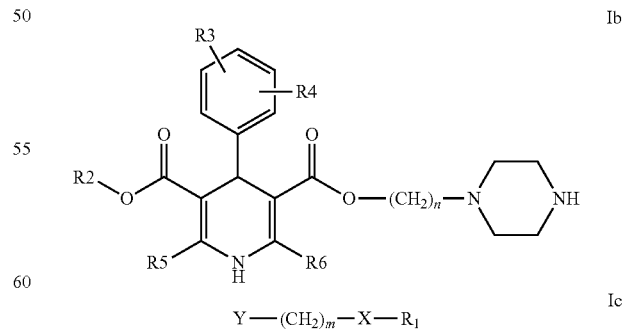

A compound of general formula Ia has a substitution reaction with a compound of general formula Id under the catalysis of NaOH; or a compound of general formula Ia has a substitution reaction with a compound of general formula Id under the catalysis of triethylamine; or a compound of general formula Ia has a substitution reaction with a compound of general formula Id directly.

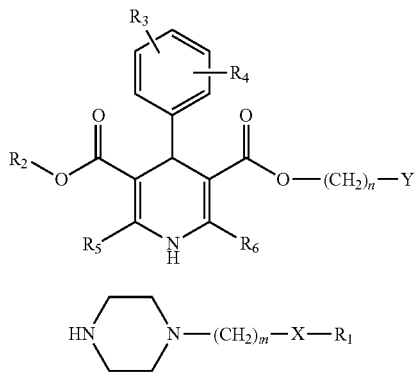

where, $R_1$, $R_2$, $R_3$, $R_4$, $R_5$, $R_6$, X, and m are defined the same as above, and Y is a halogen atom.

A preparation method of compounds of general formula (II) comprises the steps of having an addition reaction between compounds of general formulas Ib and IIa with under the catalysis of triethylamine.

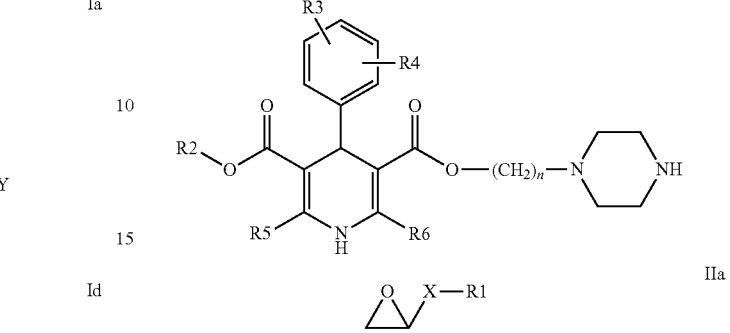

where, $R_1$, $R_2$, $R_3$, $R_4$, $R_5$, $R_6$, X, and n are defined the same as above.

A preparation method of compounds of general formula Ib comprises the step of having a substitution reaction between a compound of general formula Ia and piperazine.

The structures of some of the compounds related to the present invention are listed below:

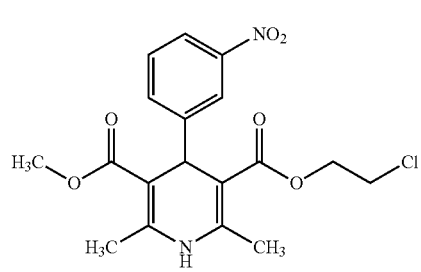

Ia₁

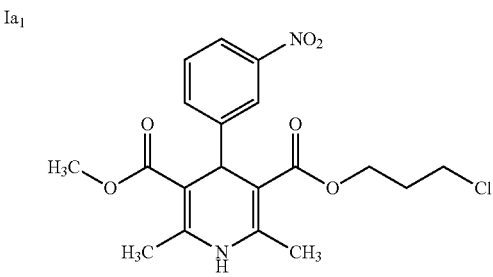

Ia₂

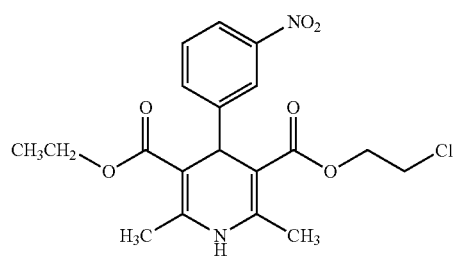

Ia₄

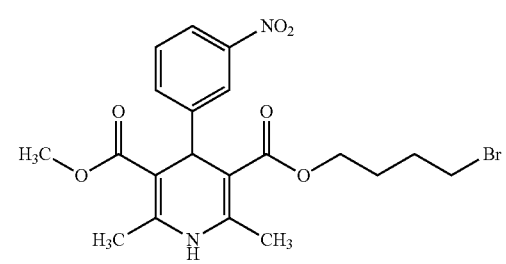

Ia₃

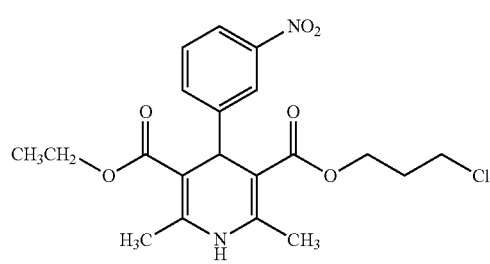

Ia₅

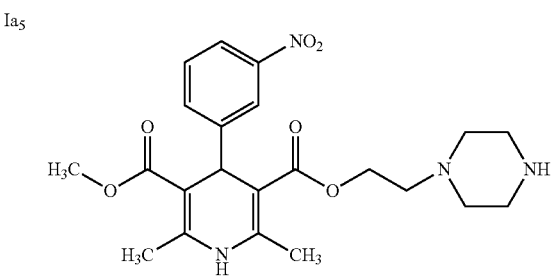

Ib₁

-continued
Ib₂
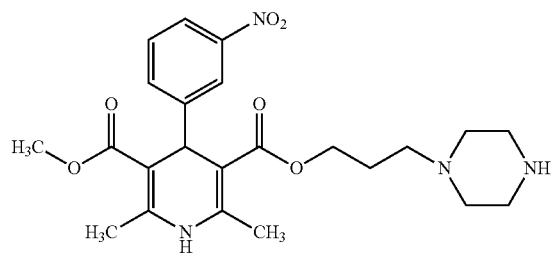
Ib₃
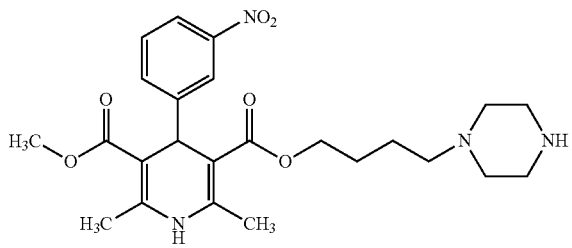
Ic₁
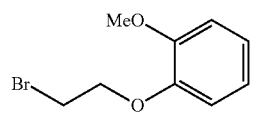
Ic₂
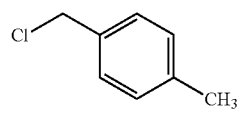
Ic₃
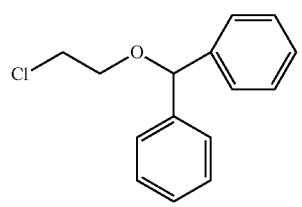
Ic₄
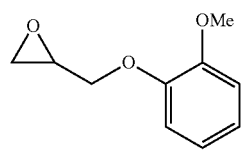
Ic₅
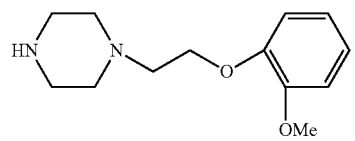
Id₁
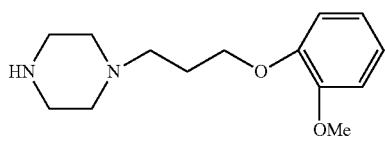
Id₂
Id₃
IIa
I1
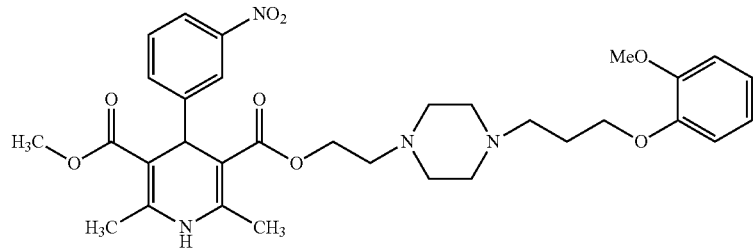
I2
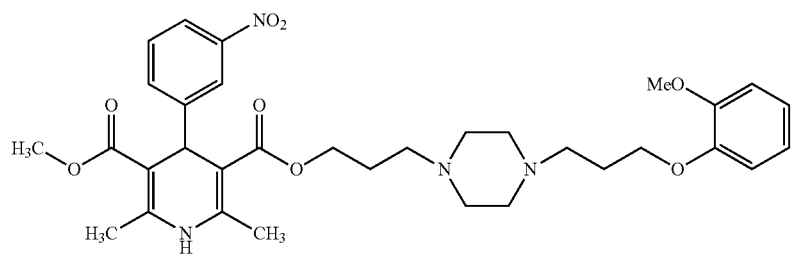

-continued
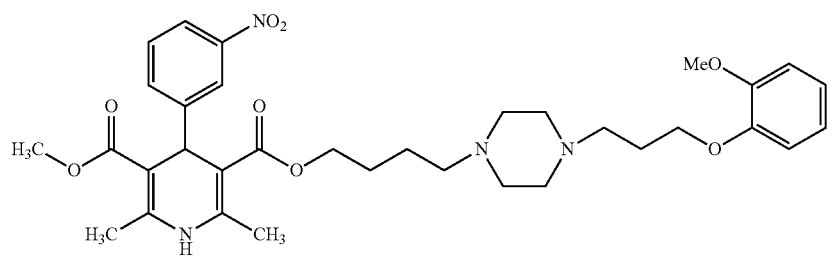
I₃
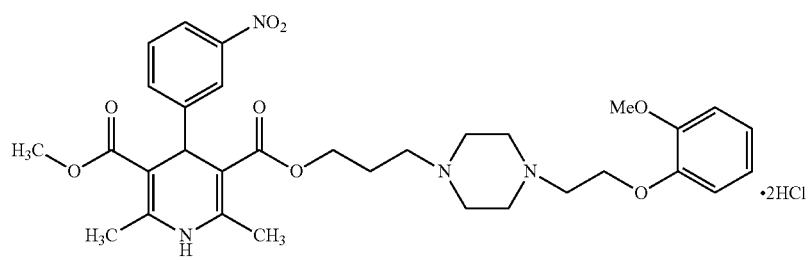
I₄
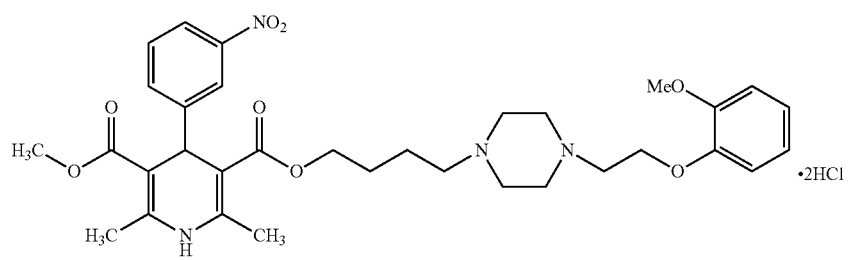
I₅
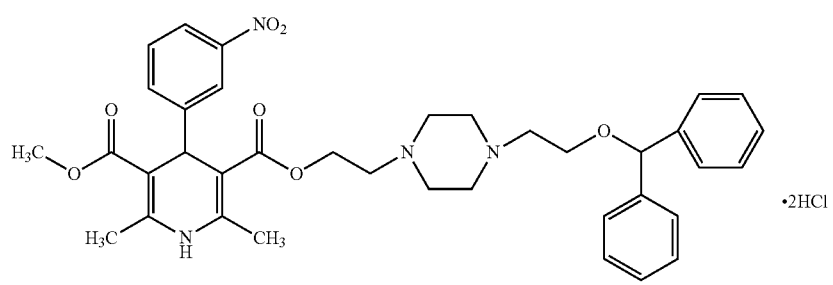
I₆
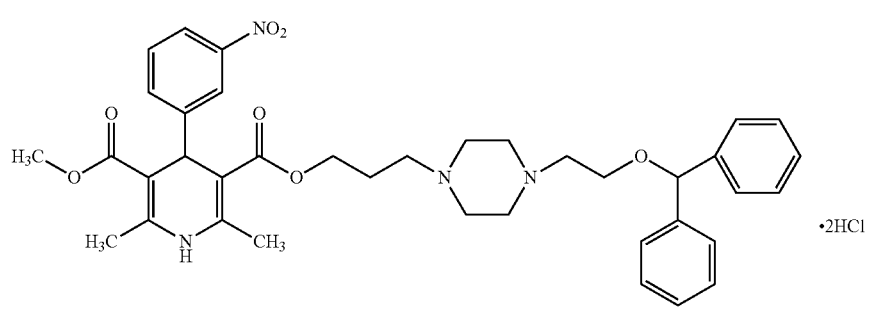
I₇
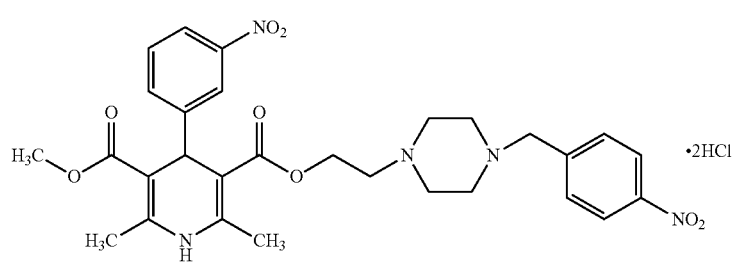
I₈

-continued
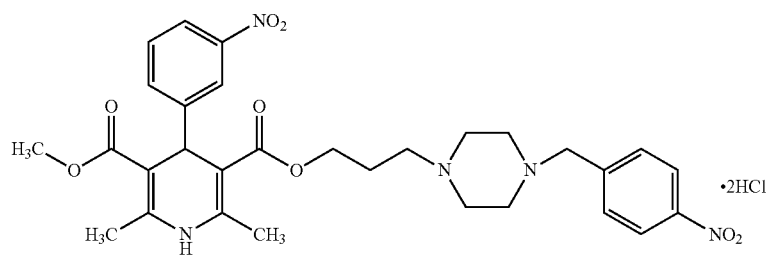
I₉
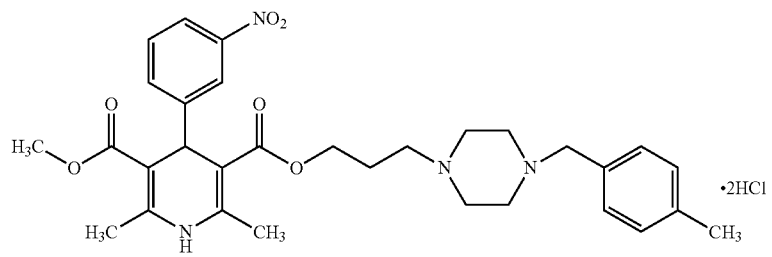
I₁₀
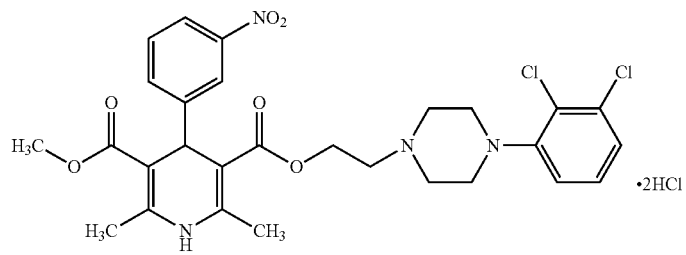
I₁₁
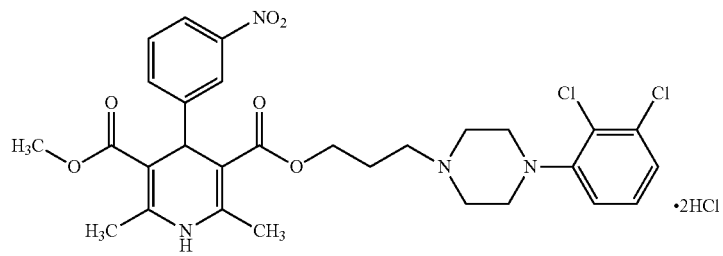
I₁₂
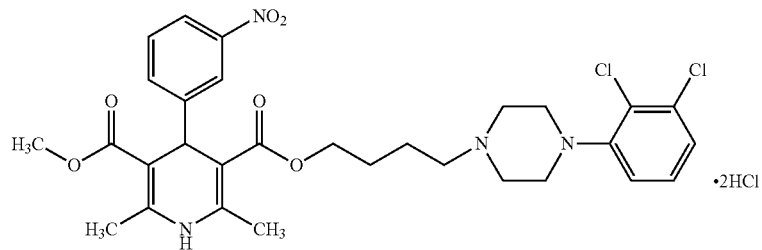
I₁₃
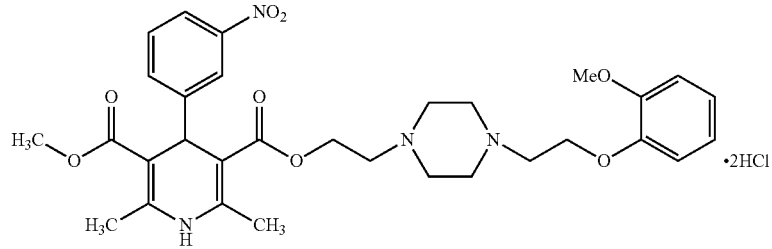
I₁₄

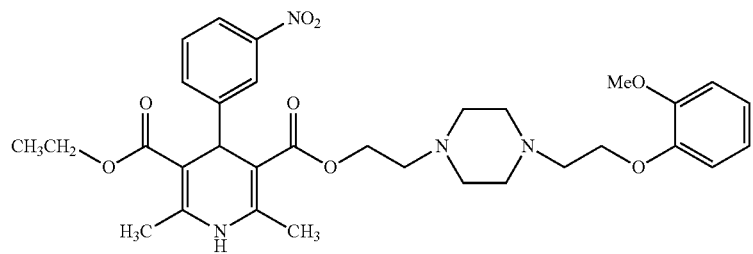
I15
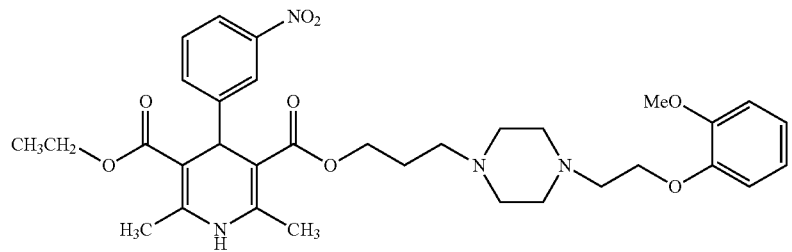
I16
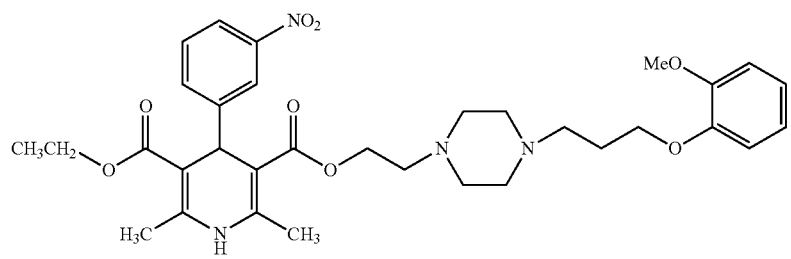
I17
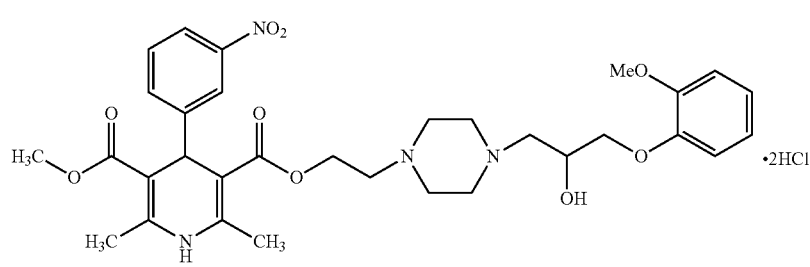
II1
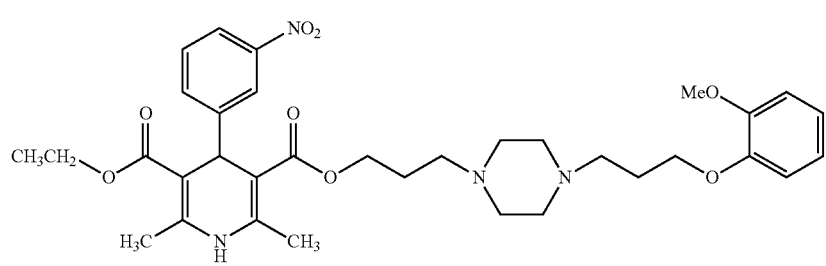
I18
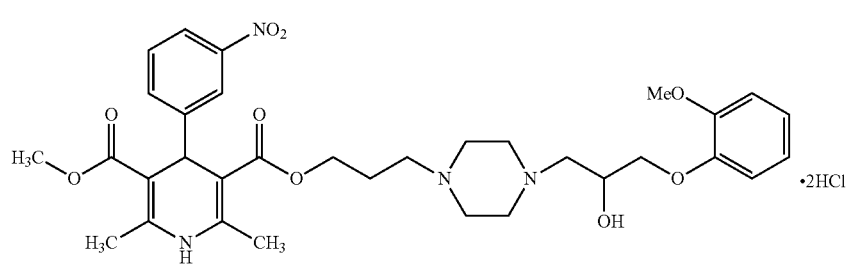
II2

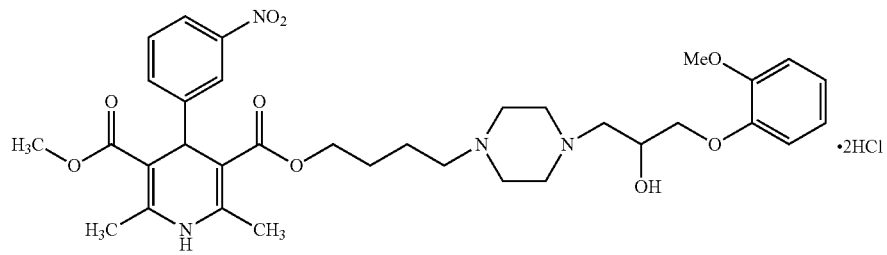

To obtain their pharmaceutical salts, a compound of general formula (I) or a compound of general formula (II) have an acid reaction to form an addition salt.

The present invention further provides a composite of cardiovascular drugs containing a compound of general formula (I) or a compound of general formula (II) or their pharmaceutical salt as an active ingredient. The pharmaceutical medicine composite contains an active ingredient and a carrier acceptable by the medicine, wherein the active ingredient constitutes 0.01-99.99% (by weight) of the composite, and the carrier acceptable by the medicine constitutes 0.01-99.99% (by weight) of the composite.

The composite can be in a form applicable for the pharmaceutical preparations, and the pharmaceutical medicine can be in a pharmaceutical form of tablets, capsules, oral liquids, mixtures, oral tablets, granules, infusions, pills, powders, plasters, circular pills, augmentins, solutions, injections, powder needle medicines, freeze-dried powder injections, suppositories, ointments, hard pastes, creams, sprays, aerosols, drops, patches, and etc.

In the pharmaceutical preparation composite of the present invention, the pharmaceutical form used for preparing a unit dosage contains an active medical ingredient of 0.1 mg-1000 mg, and each pharmaceutical preparation refers to a pharmaceutical preparation unit such as a tablet and a capsule, and it also refers to the dosage taken for each time. For example, a dosage of 100 mg is taken for each time.

If the pharmaceutical medicine composite of the present invention is prepared in a solid or semi-solid pharmaceutical form of powders, tablets, capsules, suppositories, and creams, a solid carrier can be used, wherein the solid carrier is composed of one or more substances selected from the collection of a diluent agent, a disintegrating agent, a flavoring agent, a solubilizer, a lubricant, a suspending agent, a binder, and an expander, or a packaging substance. Appropriate solid carriers include magnesium carbonate, magnesium stearate, talc, sucrose, lactose, pectin, dextrin, starch, gelatin, methyl cellulose, sodium carboxymethyl cellulose, low boiling wax, coco butter, etc. and easily provided for medications, and tablets, powders, and capsules are best oral solid pharmaceutical preparation.

The liquid pharmaceutical preparations of the present invention include solutions, suspensions and emulsions. For example, an injection of a nongastrointestinal medication can be in form of a water solution or a water-propylene glycol solution, whose permeability and pH value are adjusted to fit the physiological conditions of living organisms. The liquid pharmaceutical preparation can be made in a solution form in polyethylene glycols or water solution. The active ingredient can be dissolved in water, and then an appropriate quantity of coloring agent, flavoring agent, stabilizer and thickener can be added to prepare an oral water solution. The granular active ingredient can be spread into an adhesive substance such as natural or synthetic glue, methyl cellulose, sodium carboxymethyl cellulose and other known suspending agents for preparing an oral water suspension.

To uniformize the medication and dosage, the aforementioned pharmaceutical preparation is preferably made in the form of a dosage unit. The dosage unit of the pharmaceutical preparation refers to a physical separate unit of a single dosage, and each unit contains a predetermined quantity of active ingredients calculated for achieving an expected curing effect. The form of such dosage unit can be in a packaged form such as a tablet, a capsule, powders contained in a small tube or a small bottle, or creams, gels or paste contained in a tube or a bottle.

Although the quantity of active ingredients contained in the dosage unit form can be varied, the quantity is generally adjusted within a range of 1~800 mg according to the effect of the selected active ingredients.

The medication dosage of the present invention can be changed according to the requirements of a patient, the level of seriousness of a desired treatment, a selected compound, etc.

For the persons skilled in the art can confirm a preferred dosage for a certain particular situation according to common rules and methods. In general, the quantity used at the beginning of a treatment is less than the best dosage of an active ingredient, and then the medication dosage is increased gradually until the best treatment effect is achieved. For convenience, the total daily dosage can be divided into several parts or several times of medications, such as 1~4 times a day and 1~10 doses are taken each time.

The following experiment data show the advantages of the present invention:

The effect of compounds of the present invention to the contraction of an isolated rat's thoracic aorta ring caused by KCl is described as follows:

The present invention synthesizes 21 new DHP compounds, and some of the compounds are selected for performing pharmacological tests. With reference to Comparison of vasodilatation effect between quercetin and rutin in the isolated rat thoracic aorta authored by ZHOU Xin-mei, YAO Hui, XIA Man-li, et al, and published in Journal of Zhejiang University: Medical Sciences, 2006, 35(1), 29-33 for an embodiment.

1. Experimental Materials 1.1 Medicine and Test Sample

Control Articles: Levamlodipine Besylate, and Compounds $I_4$, $I_5$, $I_6$, $I_{14}$ and $II_2$ are provided by School of Pharmacy of China Pharmaceutical University.

Norepinephrine (Shanghai Harvest Pharmaceutical Co., Ltd) and acetylcholine (Shanghai Experiment Reagent, Plant 2), and other test samples are analyzed to be pure.

1.2 Main Instrument

The Experiment System of Bio-function (BL-410) and the Constant Temperature Smooth Muscle Trough (HW-400S) are produced by Chengdu Tme Technology Co, Ltd.

1.3 Laboratory Animal

A male SD rat, 240-260 g, supplied by Institute of Laboratory Animal Breeding and Reproduction, Qing Long Shan of Jiang Ning. Certificate of Quality No.: SCXK (So) 2002-0018.

2. Experiment Method 2.1 Preparation of Krebs Henseleit (K-H) Nutrient Solution

NaCl:118.3 mmol/L, KCl:4.7 mmol/L, $CaCl_2$: 2.5 mmol/L, $MgSO_4 \cdot 7H_2O$:1.2 mmol/L, $KH_2PO_4$:1.2 mmol/L, $NaHCO_3$:25 mmol/L, and glucose:11.1 mmol/L.

2.2 Preparation of Thoracic Aorta Ring and Measure of Tensions

Hit a male rat at its head until it faints. Quickly remove the thoracic aorta, and put it into a K-H solution passed with a mixed gas having 95% $O_2$+5% $CO_2$. Carefully remove connective tissues around the thoracic aorta and cut the blood vessel into a vascular ring of 3 mm wide. Avoid any excessive pulling to prevent damages to the endodermis. Hang the vascular ring into a bathing trough containing 30 ml of K-H liquid, and keep passing the mixed gas of 95% $O_2$+5% $CO_2$, and maintain the temperature at 37±0.5□. Adjust the rest tension to 2.0 g. Keep it in equilibrium for 2 hrs, and change the liquid once every 15 min.

Inspection of the activity of the endodermis of the blood vessel: After the thoracic aorta ring is stable, change the liquid once, and add 1 μmol/L of NA into the bathing trough. After the contraction has reached the peak value for 15 min., add 1 μmol/L of Ach. If the expected contraction of the vascular relaxation is greater than 60% after Ach is added, then the endodermis is considered to be complete, or else the endodermis will be damaged.

A thoracic aorta ring with a complete endodermis is selected for conducting the experiment. After the changed liquid is stable, Add 80 mmol/L KCl to induce the maximum contraction amplitude, sequentially accumulate the medications, such that the medicine concentrations are 0.05 μmol/L, 0.1 μmol/L, 0.5 μmol/L, 1 μmol/L, 2 μmol/L, 4 μmol/L, and 10 μmol/L respectively. Record the change of tensions. The vascular relaxation level is indicated by the inhibition rate. In other words, KCl induces a difference of values between the maximum tension of the contraction and the vascular tension after medicines with different concentrations are added. The ratio of differences of the values to the maximum contraction amplitude induced by KCl reflects the level of vascular relaxation. The sample size of the arota rings for each medicine group is 6. In other words, the experiment is performed repeatedly for 6 times.

3. Experiment Results

In Table 1, compounds $I_4$, $I_5$, $I_6$, $I_{14}$, $II_2$ has an inhibition effect to the contraction of a vascular ring with complete endodermis caused by KCl, and $IC_{50}$ values are equal to 2.0, 0.5, 1.9, 0.2, 0.8 μmol/L respectively, which are smaller than the $IC_{50}$ value (4.1 μmol/L) of the control article (Levamlodipine Besylate). Obviously, the activities of $I_4$, $I_5$, $I_6$, $I_{14}$, and $II_2$ are greater than that of the control article (Levamlodipine Besylate), wherein $I_5$ and $I_{14}$ have the strongest activities.

Table 1. Effects of compounds to the contraction of an isolated rat's thoracic aorta ring caused by KCl ($\bar{x}\pm S$, n=6)

| Group | 0.05 μmol/L | 0.1 μmol/L | 0.5 μmol/L | 1 μmol/L | 2 μmol/L | 4 μmol/L | 10 μmol/L |
|---|---|---|---|---|---|---|---|
| Control | | 4.5 ± 0.6 | 18.4 ± 2.6 | 37.7 ± 3.6 | 46.8 ± 4.1 | 69.0 ± 5.9 | 84.6 ± 6.1 |
| $I_4$ | | 13.2 ± 1.3 | 20.5 ± 2.2 | 33.8 ± 2.8 | 59.4 ± 4.0 | 62.4 ± 4.8 | 72.0 ± 4.7 |
| $I_5$ | | 24.5 ± 3.2 | 47.9 ± 3.9 | 66.0 ± 4.0 | 75.0 ± 3.5 | 91.6 ± 3.2 | 100.1 ± 3.0 |
| $I_6$ | | 9.3 ± 1.0 | 20.5 ± 2.5 | 33.7 ± 2.4 | 49.7 ± 3.5 | 66.9 ± 3.6 | 79.0 ± 4.5 |
| $I_{14}$ | 27.4 ± 3.4 | 35.7 ± 3.0 | 62.9 ± 6.8 | 81.7 ± 3.3 | 96.2 ± 4.5 | 101.1 ± 3.4 | |
| $II_2$ | | 11.0 ± 1.5 | 32.2 ± 3.0 | 50.7 ± 5.7 | 65.2 ± 4.2 | 93.4 ± 3.1 | 101.2 ± 3.2 |

Other compounds have the same or similar biological activity, and they are not listed one by one here.

The compounds or their pharmaceutical salts in accordance with the present invention show an excellent receptor combining capability in the treatment of cardiovascular diseases, so as to achieve the effects of extending the metabolism, improving the bio-availability, reducing the side effects, and providing the value of extensive applications.

DETAILED DESCRIPTION OF THE PREFERRED EMBODIMENTS

The technical characteristics of the present invention will become apparent with the detailed description of preferred embodiments and the illustration of related drawings as follows.

The following embodiments are provided for illustrating the present invention, but not intended for limiting the scope of the present invention.

Preferred Embodiment 1

1,4-dihydro-2,6-dimethyl-4-(3-nitrophenyl)-3,5-pyridinecarboxylic acid methyl ester 2-(N-1-piperazinyl)ethyl ester ($Ib_1$)

1,4-dihydro-2,6-dimethyl-4-(3-nitrophenyl)-3,5-pyridinecarboxylic acid methyl ester 2-chloroethyl ester ($Ia_1$): 11.84 g (30 mmol), piperazine (anhydrous) 7.76 g (90 mmol), acetonitrile 60 ml are blended, and then refluxed for 3 hrs, and a pressure reduction contraction is performed, and dichloromethane (40 ml) is added, blended, and rinsed by water, dried by sodium sulfate (anhydrous), blended, rinsed by water, filtered, and a pressure reduction and a concentration process are performed to the filtered liquid, and a remnant silicone tubing chromatography (ethylacetate: acetone, 3:1) is used for separating and obtaining a light yellow solid (8.66 g) with a yield rate of 65%, mp 166~169□.

1,4-dihydro-2,6-dimethyl-4-(3-nitrophenyl)-3,5-pyridinecarboxylic acid methyl ester3-(N-1-piperazinyl) propyl ester (Ib$_2$), 1,4-dihydro-2,6-dimethyl-4-(3-nitrophenyl)-3,5-pyridinecarboxylic acid methyl ester 4-(N-1-piperazinyl) butyl ester (Ib$_3$)

Refer to the Ib$_1$ synthesis method for the synthesis.

Preferred Embodiment 2

1,4-dihydro-2,6-dimethyl-4-(3-nitrophenyl)-3,5-pyridinecarboxylic acid methyl ester 2-(N-4-(3-(2-methoxyphenoxy)propyl)piperazinyl)ethyl ester (I$_1$)

Compounds Ib$_1$ 1.33 g (0.003 mol), Ic$_2$ 0.602 g (0.003 mol), sodium hydroxide 0.12 g (0.003 mol), and toulene 10 ml are blended, and then refluxed for 2 hrs, and a pressure reduction and a concentration process are performed, and dichloromethane (10 ml) is added, blended, and rinsed by water, and the organic layer is dried by sodium sulfate (anhydrous) and filtered, and the pressure reduction and concentration process are performed to the filtered liquid, and the remnant silicone tubing chromatography (petroleum ether: ethylacetate, 7:1) is used for separating and obtaining a yellow oil 1.30 g with a yield rate of 71%.

ESI-MS (m/z):609.3 [M+H]$^+$

IR (cm$^{-1}$):3550, 3340, 3085, 2961, 2924, 2852, 2816, 1700, 1528, 1503, 1457, 1348, 1260, 1212, 1095, 1020, 802, 704, 702, 678

$^1$H-NMR (CDCl$_3$): δ1.99 (2H, m, —NCH$_2$CH$_2$CH$_2$O), 2.34 (6H, s, C$_{2-6}$—CH$_3$), 2.46-2.58 (12H, m, —COOCH$_2$CH$_2$N, piperazidine-H, —NCH$_2$CH$_2$CH$_2$O), 3.61 (3H, s, —COOCH$_3$), 3.82 (3H, s, —OCH$_3$), 4.02-4.16 (4H, m, —COOCH$_2$, —CH$_2$O), 5.07 (1H, s, C$_4$—H), 5.75 (1H, brs, —NH), 6.87 (4H, m, methoxyphenyl-H), 7.33 (1H, t, Nitrophenyl 5-H), 7.6 (1H, d, Nitrophenyl 6-H), 7.98 (1H, d, Nitrophenyl 4-H), 8.06 (1H, m, Nitrophenyl 2-H).

Preferred Embodiment 3

1,4-dihydro-2,6-dimethyl-4-(3-nitrophenyl)-3,5-pyridinecarboxylic acid methyl ester3-(N-4-(3-(2-methoxyphenoxy)propyl)piperazinyl)propyl ester (I$_2$)

With reference to the I$_1$ synthesis method, the aforementioned compound is prepared by Ib$_2$ and Ic$_2$, with a yield of 65.5%.

ESI-MS (m/z):623.3 [M+H]$^+$

IR (cm$^{-1}$):3344, 2963, 2815, 1700, 1528, 1504, 1348, 1261, 1069, 1020, 800, 742, 703

$^1$H-NMR (CDCl$_3$): δ1.79 (2H, m, —COOCH$_2$CH$_2$CH$_2$N), 2.04 (2H, m, —NCH$_2$CH$_2$CH$_2$O), 2.27 (2H, t, —COOCH$_2$CH$_2$CH$_2$N), 2.32 (6H, s, C$_{2-6}$—CH$_3$), 2.46-2.58 (10H, m, piperazidine-H, —NCH$_2$CH$_2$CH$_2$O), 3.64 (3H, s, —COOCH$_3$), 3.85 (3H, s, —OCH$_3$), 4.02-4.16 (4H, m, —COOCH$_2$, —CH$_2$O), 5.07 (1H, s, C$_4$—H), 5.86 (1H, brs, —NH), 6.89 (4H, m, methoxyphenyl-H), 7.33 (1H, t, Nitrophenyl 5-H), 7.6 (1H, d, Nitrophenyl 6-H), 7.98 (1H, d, Nitrophenyl 4-H), 8.09 (1H, m, Nitrophenyl 2-H).

Preferred Embodiment 4

1,4-dihydro-2,6-dimethyl-4-(3-nitrophenyl)-3,5-pyridinecarboxylic acid methyl ester 4-(N-4-(3-(2-methoxyphenoxy)propyl)piperazinyl) butyl ester (I$_3$)

With reference to the I$_1$ synthesis method, the aforementioned compound is prepared by Ib$_3$ and Ic$_2$ with a yield of 69.7%.

ESI-MS (m/z):637.3 [M+H]$^+$

IR (cm$^{-1}$):3344, 3080, 2963, 2814, 1701, 1530, 1506, 1350, 1262, 1213, 1020, 805, 741, 703

$^1$H-NMR (CDCl$_3$): δ1.48 (2H, m, —COOCH$_2$CH$_2$CH$_2$CH$_2$N), 1.61 (2H, m, —COOCH$_2$CH$_2$CH$_2$CH$_2$N), 2.02 (2H, m, —NCH$_2$CH$_2$CH$_2$O), 2.29 (2H, t, —COOCH$_2$CH$_2$CH$_2$CH$_2$N), 2.36 (6H, s, C$_{2-6}$—CH$_3$), 2.50-2.60 (10H, m, piperazidine-H, —NCH$_2$CH$_2$CH$_2$O), 3.64 (3H, s, —COOCH$_3$), 3.85 (3H, s, —OCH$_3$), 4.02-4.16 (4H, m, —COOCH$_2$, —CH$_2$O), 5.08 (1H, s, C$_4$—H), 5.86 (1H, brs, —NH), 6.90 (4H, m, methoxyphenyl-H), 7.37 (1H, t, Nitrophenyl 5-H), 7.6 (1H, d, Nitrophenyl 6-H), 7.98 (1H, d, Nitrophenyl-4-H), 8.09 (1H, m, Nitrophenyl 2-H).

Preferred Embodiment 5

1,4-dihydro-2,6-dimethyl-4-(3-nitrophenyl)-3,5-pyridinecarboxylic acid methyl ester 3-(N-4-(2-(2-methoxyphenoxy)ethyl)piperazinyl)propyl ester hydrochloride (I$_4$)

Compounds Ib$_2$ 1.37 g (0.003 mol), Ic$_1$ 0.693 g (0.003 mol), sodium hydroxide 0.12 g (0.003 mol), and toulene 10 ml are blended, and then reacted at 60□ for 1 hr, and the pressure reduction and concentration process are performed, and dichloromethane (10 ml) is added, blended, and rinsed by water, and the organic layer is dried by sodium sulfate (anhydrous) and filtered, and the pressure reduction and concentration process are performed to the filtered liquid, and the remnant silicone tubing chromatography (petroleum ether: ethylacetate, 8:1) is used for separating and obtaining a yellow oil, soluble in ethyl ether (anhydrous) 5 ml, and dry HCl at room temperature is passed into the solution until the pH value of the solution is 2, and then filtered, and dried to obtain a light yellow powder 1.53 g with a yield rate of 75%, and amp of 173~175□.

ESI-MS (m/z):609.3 [M+H]$^+$

IR (cm$^{-1}$):3424, 2950, 2837, 1693, 1527, 1503, 1349, 1254, 1213, 1120, 1095, 1018, 745, 705

$^1$H-NMR (CDCl$_3$): δ1.81 (2H, m, —COOCH$_2$CH$_2$CH$_2$N), 2.31 (2H, t, —COOCH$_2$CH$_2$CH$_2$N), 2.37 (6H, s, C2,6-CH$_3$), 2.44 (4H, brs, —CH$_2$NCH$_2$), 2.61 (4H, brs, —CH$_2$NCH$_2$), 2.84 (2H, t, —NCH$_2$CH$_2$O), 3.64 (3H, s, —COOCH$_3$), 3.85 (3H, s, —OCH$_3$), 4.12 (4H, m, —COOCH$_2$, —CH$_2$O), 5.08 (1H, s, C$_4$—H), 5.73 (1H, brs, —NH), 6.90 (4H, m, methoxyphenyl-H), 7.37 (1H, t, Nitrophenyl 5-H), 7.62 (1H, d, Nitrophenyl 6-H), 7.98 (1H, d, Nitrophenyl 4-H), 8.09 (1H, m, Nitrophenyl 2-H).

Preferred Embodiment 6

1,4-dihydro-2,6-dimethyl-4-(3-nitrophenyl)-3,5-pyridinecarboxylic acid methyl ester-4-(N-4-(2-(2-methoxyphenoxy)ethyl)piperazinyl)butyl ester hydrochloride (I$_5$)

With reference to the I$_4$ synthesis method, it is prepared by Ib$_3$ and Ic$_1$, with a yield of 73%, and amp of 163~166□.

ESI-MS (m/z):623.3 [M+H]$^+$

IR (cm$^{-1}$):3426, 2949, 1692, 1502, 1348, 1254, 1215, 1122, 1020, 746

$^1$H-NMR (CDCl$_3$): δ1.45 (2H, m, —COOCH$_2$CH$_2$CH$_2$CH$_2$N), 1.61 (2H, m, —COOCH$_2$CH$_2$CH$_2$CH$_2$N), 2.31 (2H, t, —COOCH$_2$CH$_2$CH$_2$CH$_2$N), 2.36 (6H, s, C$_{2-6}$—CH$_3$), 2.45 (4H, brs, —CH$_2$NCH$_2$), 2.61 (4H, brs, —CH$_2$NCH$_2$), 2.85 (2H, t, —NCH$_2$CH$_2$O), 3.64 (3H, s, —COOCH$_3$), 3.85 (3H, s, —OCH$_3$), 4.05 (2H, m, —COOCH$_2$), 4.15 (2H, t, —CH$_2$O), 5.08 (1H, s, C$_4$—H), 5.74 (1H, brs, —NH), 6.90 (4H, m, methoxyphenyl-H), 7.36 (1H, t, Nitrophenyl 5-H), 7.61 (1H, d, Nitrophenyl 6-H), 7.98 (1H, d, Nitrophenyl 4-H), 8.09 (1H, m, Nitrophenyl 2-H).

Preferred Embodiment 7

1,4-dihydro-2,6-dimethyl-4-(3-nitrophenyl)-3,5-pyridinecarboxylic acid methyl ester2-(N-4-(diphenylmethoxy ethyl)piperazinyl)ethyl ester hydrochloride (I$_6$)

Compounds Ib$_1$ 1.33 g (0.003 mol), Ic$_3$ 0.738 g (0.003 mol), and toulene (10 ml) are blended, and 6N NaOH solution (0.5 ml) is added and reacted at 80□ for 2 hrs, and the pressure reduction and concentration process are performed, and dichloromethane (10 ml) is added, blended, and rinsed by water, and the organic layer is dried by sodium sulfate (anhydrous) and filtered, and the pressure reduction and concentration process are performed to the filtered liquid, and the remnant silicone tubing chromatography (petroleum ether:ethylacetate, 8:1) is used for separating and obtaining a yellow oil soluble in ethyl ether (anhydrous) 5 ml, and dry HCl gas at room temperature is passed into the solution until pH=2, and filtered and dried to obtain a light yellow powder (0.63 g) with a yield rate of 31.9%, and amp of 170~173□.

ESI-MS (m/z): 655.3 [M+H]$^+$

IR (cm$^{-1}$):3402, 3198, 2949, 2422, 1694, 1526, 1490, 1348, 1213, 1019, 744, 703

$^1$H-NMR (CDCl$_3$): δ2.30-2.70 (18H, m, —COOCH$_2$CH$_2$N, C$_{2-6}$—CH$_{3,2}$×-NCH$_2$CH$_2$N, —NCH$_2$CH$_2$O), 3.58 (2H, t, —CH$_2$O), 3.63 (3H, s, —COOCH$_3$), 4.13 (2H, m, —COOCH$_2$CH$_2$N), 5.09 (1H, s, C$_4$—H), 5.37 (1H, s, —CHO), 5.70 (1H, brs, —NH), 7.20-7.40 (11H, t, m-Nitrophenyl 5-H, Diphenylmethyl-H), 7.65 (1H, d, m-Nitrophenyl 6-H), 7.98 (1H, d, m-Nitrophenyl 4-H), 8.09 (1H, s, m-Nitrophenyl 2-H).

Preferred Embodiment 8

1,4-dihydro-2,6-dimethyl-4-(3-nitrophenyl)-3,5-pyridinecarboxylic acid methyl ester 3-(N-4-(diphenylmethoxy ethyl)piperazinyl)propyl ester hydrochloride (I$_7$)

With reference to the I$_6$ synthesis method, the aforementioned compound is prepared by Ib$_2$ and Ic$_3$ with a yield of 32.2%, and a mp of 159~162□.

ESI-MS (m/z):669.3 [M+H]$^+$

IR (cm$^{-1}$):3408, 3201, 3064, 2949, 2837, 2442, 1692, 1526, 1491, 1348, 1214, 1118, 1019, 745, 704

$^1$H-NMR (CDCl$_3$): δ1.79 (2H, m, —COOCH$_2$CH$_2$CH$_2$), 2.30-2.64 (16H, m, —COOCH$_2$CH$_2$CH$_2$, C$_{2-6}$—CH$_{3,2}$×-NCH$_2$CH$_2$N), 2.71 (2H, t, —NCH$_2$CH$_2$O), 3.59 (2H, t, —CH$_2$O), 3.64 (3H, s, —COOCH$_3$), 4.07 (2H, m, —COOCH$_2$CH$_2$CH$_2$), 5.08 (1H, s, C$_4$—H), 5.37 (1H, s, —CHO), 5.82 (1H, br, —NH), 7.20-7.40 (11H, m, m-Nitrophenyl 5-H, Diphenylmethyl-H), 7.61 (1H, d, m-Nitrophenyl 6-H), 7.99 (1H, d, m-Nitrophenyl 4-H), 8.09 (1H, s, m-Nitrophenyl 2-H).

Preferred Embodiment 9

1,4-dihydro-2,6-dimethyl-4-(3-nitrophenyl)-3,5-pyridinecarboxylic acid methyl ester 2-(N-4-(4-nitrobenzl)piperazinyl)ethyl ester hydrochloride (I$_8$)

compound Ib$_1$ 2.22 g (0.005 mol), Ic$_4$ 1.08 g (0.005 mol), sodium hydroxide 0.2 g (0.005 mol), and dichloromethane (10 ml) are blended and then refluxed for 1 hr, and the reacting liquid is rinsed by water, and dried by sodium sulfate (anhydrous), filtered, and the pressure reduction and concentration process are performed to the filtered liquid, and the remnant silicone tubing chromatography (petroleum ether:ethylacetate, 8:1) is used for separating and obtaining a yellow oil soluble in ethyl ether (anhydrous) 5 ml, and dry HCl gas at room temperature is passed into the solution until pH=2, and filtered, and dried to obtain a light yellow powder (1.70 g) with a yield rate of 52.3%, and a mp of 182~185□.

ESI-MS (m/z):580.3 [M+H]$^+$

IR (cm$^{-1}$):3373, 2956, 2874, 2815, 2773, 1698, 1528, 1513, 1340, 1210, 1094, 1010, 742, 709

$^1$H-NMR (CDCl$_3$): δ2.36-2.60 (16H, m, —COOCH$_2$CH$_2$N, C$_{2-6}$—CH$_3$, piperazidine-H), 3.57 (2H, s, —CH$_2$-p-Nitrophenyl), 3.65 (3H, s, —COOCH$_3$), 4.12-4.19 (2H, m, —COOCH$_2$CH$_2$N), 5.10 (1H, s, C$_4$—H), 5.72 (1H, brs, —NH), 7.36 (1H, t, m-Nitrophenyl 5-H, Diphenylmethyl-H), 7.49 (2H, d, p-Nitrophenyl 2-H, 6-H), 7.64 (1H, d, m-Nitrophenyl 6-H), 7.98 (1H, d, m-Nitrophenyl 4-H), 8.01 (1H, s, m-Nitrophenyl 2-H), 8.17 (2H, d, p-Nitrophenyl 3-H, 5-H).

Preferred Embodiment 10

1,4-dihydro-2,6-dimethyl-4-(3-nitrophenyl)-3,5-pyridinecarboxylic acid methyl ester 3-(N-4-(4-nitrobenzl)piperazinyl) propyl ester hydrochloride (I$_9$)

With reference to the I$_8$ synthesis method, the aforementioned compound is prepared by Ib$_2$ and Ic$_4$ with a yield rate of 42.3%, and a mp of 170~171□.

ESI-MS (m/z): 616.2 [M+Na]$^+$

IR (cm$^{-1}$):3424, 2954, 1690, 1525, 1487, 1349, 1215, 807, 742

$^1$H-NMR (CDCl$_3$): δ1.78 (2H, q, —COOCH$_2$CH$_2$CH$_2$N), 2.31-2.60 (16H, m, —COOCH$_2$CH$_2$CH$_2$N, C2,6-CH$_{3,2}$×-NCH$_2$CH$_2$N), 3.58 (2H, s, —CH$_2$-p-Nitrophenyl), 3.65 (3H, s, —COOCH$_3$), 4.09 (2H, m, —COOCH$_2$CH$_2$CH$_2$N), 5.08 (1H, s, C$_4$—H), 5.85 (1H, brs, —NH), 7.37 (1H, t, m-Nitrophenyl 5-H), 7.49 (2H, d, p-Nitrophenyl 2-H, 6-H), 7.62 (1H, d, m-Nitrophenyl 6-H), 7.98 (1H, d, m-Nitrophenyl 4-H), 8.10 (1H, s, m-Nitrophenyl 2-H), 8.16 (2H, d, p-Nitrophenyl 3-H, 5-H).

Preferred Embodiment 11

1,4-dihydro-2,6-dimethyl-4-(3-nitrophenyl)-3,5-pyridinecarboxylic acid methyl ester 3-(N-4-(4-methylbenzl)piperazinyl) propyl ester hydrochloride (I$_{10}$)

With reference to the I$_8$ synthesis method, the aforementioned compound is prepared by Ib$_2$ and Ic$_5$, with a yield of 32.7%, and a mp of 163~165 □.

ESI-MS (m/z):563.3[M+H]$^+$

IR (cm$^{-1}$):3424, 2954, 1690, 1525, 1487, 1349, 1215, 807, 742

$^1$H-NMR (CDCl$_3$): δ1.56 (3H, s, —CH$_3$), 1.77 (2H, q, —COOCH$_2$CH$_2$CH$_2$N), 2.30-2.60 (16H, m, —COOCH$_2$CH$_2$CH$_2$N, C$_{2-6}$—CH$_3$,2×-NCH$_2$CH$_2$N), 3.45 (2H, s, —CH$_2$-p-Methylphenyl), 3.65 (3H, s, —COOCH$_3$), 4.10 (2H, m, —COOCH$_2$CH$_2$CH$_2$N), 5.09 (1H, s, C4-H), 5.68 (1H, brs, —NH), 7.15 (4H, m, p-Methylphenyl 2-H, 3-H, 5-H, 6-H), 7.43 (1H, s, m-Nitrophenyl 5-H), 7.62 (1H, d, m-Nitrophenyl 6-H), 8.00 (1H, d, m-Nitrophenyl 4-H), 8.09 (1H, s, m-Nitrophenyl 2-H).

Preferred Embodiment 12

1,4-dihydro-2,6-dimethyl-4-(3-nitrophenyl)-3,5-pyridinecarboxylic acid methyl ester2-(N-4-(2,3-dichlorophenyl)piperazinyl)ethyl ester (I$_{11}$)

Compounds Ia$_1$ 1.97 g (0.005 mol), Id$_1$ hydrochloride 1.52 g (0.005 mol), triethylamine (0.2 ml) are refluxed in toulene for 2 hrs, and the pressure reduction and concentration process are performed, and dichloromethane (20 ml) and 1N NaOH solution (10 ml) are added and blended, and the organic layer is rinsed by water to neutral, and dried by sodium sulfate (anhydrous), and filtered, and the pressure reduction and concentration process are performed to the filtered liquid, and the remnant silicone tubing chromatography (petroleum ether:ethylacetate, 6:1) is used for separating and obtaining a yellow solid (1.80 g) with a yield rate of 61.0%, and amp of 115~120□.

ESI-MS (m/z):589.2 [M+H]$^+$

IR (cm$^{-1}$):3441, 3258, 3221, 3100, 2953, 1704, 1681, 1529, 906, 710

$^1$H-NMR (CDCl$_3$): δ2.39 (6H, d, C$_{2-6}$—CH$_3$), 2.67 (6H, m, —COOCH$_2$CH$_2$N, —CH$_2$NCH$_2$), 3.01 (4H, s, —CH$_2$NCH$_2$), 3.65 (3H, s, —COOCH$_3$), 4.20 (2H, m, —COOCH$_2$), 5.12 (1H, s, C$_4$—H), 5.71 (1H, brs, —NH), 6.93 (1H, m, Dichlorophenyl 5-H), 7.14 (2H, m, Dichlorophenyl 4-H, 6-H), 7.38 (1H, t, m-Nitrophenyl 5-H), 7.66 (1H, d, m-Nitrophenyl 6-H), 7.99 (1H, d, m-Nitrophenyl 4-H), 8.11 (1H, m, m-Nitrophenyl 2-H).

Preferred Embodiment 13

1,4-dihydro-2,6-dimethyl-4-(3-nitrophenyl)-3,5-pyridinecarboxylic acid methyl ester 3-(N-4-(2,3-dichlorophenyl)piperazinyl)propyl ester hydrochloride (I$_{12}$)

Compounds Ia$_2$ 2.04 g (0.005 mol), Id$_1$ hydrochloride 1.52 g (0.005 mol), triethylamine (0.2 ml) are refluxed in toulene (20 ml) for 2 hrs, and the pressure reduction and concentration process are performed, and dichloromethane (20 ml) and 1N NaOH solution (10 ml) are added and blended, and the organic layer is rinsed by water to neutral, and dried by sodium sulfate (anhydrous) and filtered, and the pressure reduction and concentration process are performed, and the remnant silicone tubing chromatography (petroleum ether: ethylacetate, 6:1) is used for separating and obtaining a yellow solid soluble in ethyl ether (anhydrous) 10 ml, and dry HCl gas at room temperature is passed into the solution until pH=2, and filtered and dried to obtain a light yellow powder (1.79 g) with a yield rate of 53.1%, and a mp of 178-180□.

ESI-MS (m/z):603.2[M+H]$^+$

IR (cm$^{-1}$):3416, 2950, 1693, 1526, 1348, 1213, 956, 699

$^1$H-NMR (CDCl$_3$): δ2.36 (6H, d, C$_{2-6}$—CH$_3$), 2.45 (2H, m, —COOCH$_2$CH$_2$CH$_2$N), 2.65 (4H, s, —CH$_2$NCH$_2$CH$_2$), 3.09 (4H, s, —CH$_2$NCH$_2$), 3.65 (3H, s, —COOCH$_3$), 4.12 (2H, m, —COOCH$_2$), 5.10 (1H, s, C$_4$—H), 5.85 (1H, brs, —NH), 6.93 (1H, m, 2,3-Dichlorophenyl 5-H), 7.14 (2H, m, 2,3-Dichlorophenyl 4-H&6-H), 7.38 (1H, t, m-Nitrophenyl 5-H), 7.63 (1H, d, m-Nitrophenyl 6-H), 7.99 (1H, d, m-Nitrophenyl 4-H), 8.11 (1H, m, m-Nitrophenyl 2-H).

Preferred Embodiment 14

1,4-dihydro-2,6-dimethyl-4-(3-nitrophenyl)-3,5-pyridinecarboxylic acid methyl ester 4-(N-4-(2,3-dichlorophenyl)piperazinyl)butyl ester hydrochloride (I$_{13}$)

With reference to the I$_{12}$ synthesis method, it is prepared by Ia$_3$ and Id$_1$, with a yield of 66.0%, and a mp of 170-173□.

ESI-MS (m/z):617.3 [M+H]$^+$

IR (cm$^{-1}$):3363, 2954, 2827, 1702, 1652, 1527, 1348, 1215, 949, 781, 709

$^1$H-NMR (CDCl$_3$): δ1.49 (2H, m, —COOCH$_2$CH$_2$CH$_2$CH$_2$N), 1.65 (2H, m, —COOCH$_2$CH$_2$CH$_2$CH$_2$N), 2.38 (8H, m, C$_{2-6}$—CH$_3$, —COOCH$_2$CH$_2$CH$_2$CH$_2$N), 2.58 (4H, s, —CH$_2$NCH$_2$), 3.05 (4H, brs, —CH$_2$NCH$_2$), 3.65 (3H, s, —COOCH$_3$), 4.06 (2H, m, —COOCH$_2$CH$_2$CH$_2$CH$_2$N), 5.10 (1H, s, C$_4$—H), 5.72 (1H, brs, —NH), 6.95 (1H, m, Dichlorophenyl 5-H), 7.14 (2H, m, Dichlorophenyl 4,6-H), 7.37 (1H, t, m-Nitrophenyl 5-H), 7.64 (1H, d, m-Nitrophenyl 6-H), 7.99 (1H, d, m-Nitrophenyl 4-H), 8.11 (1H, m, m-Nitrophenyl 2-H).

Preferred Embodiment 15

1,4-dihydro-2,6-dimethyl-4-(3-nitrophenyl)-3,5-pyridinecarboxylic acid methyl ester2-(N-4-(2-(2-methoxyphenoxy)ethyl)piperazinyl)ethyl ester hydrochloride (I$_{14}$)

Compounds Ia$_1$ 1.97 g (0.005 mol), Id$_2$ 1.19 g (0.005 mol), sodium hydroxide 0.2 g (0.005 mol), and acetonitrile (15 ml) are blended and reacted at 60□ for 1 hr, and the pressure reduction and concentration process are performed, and dichloromethane (15 ml) and water (15 ml) are added and blended, and the organic layer is dried by sodium sulfate (anhydrous) and filtered, and the pressure reduction and concentration process are performed to the filtered liquid, and the remnant silicone tubing chromatography (petroleum ether: ethylacetate, 8:1) is used for separating and obtaining a yellow oil soluble in ethyl ether (anhydrous) 5 ml, and dry HCl gas at room temperature is passed into the solution until pH=2, and filtered and dried to obtain a light yellow powder (1.25 g) with a yield rate of 37.6%, and amp of 112-115 □.

ESI-MS (m/z):595.3 [M+H]$^+$

IR (cm$^{-1}$):3409, 3197, 2951, 1696, 1503, 1215, 1123, 748

$^1$H-NMR (CDCl$_3$): δ1.99 (2H, m, —COOCH$_2$CH$_2$N), 2.37 (6H, s, C$_{2-6}$—CH$_3$), 2.59 (8H, m, 2×-NCH$_2$CH$_2$N), 2.83 (2H, t, —NCH$_2$CH$_2$O), 3.64 (3H, s, —COOCH$_3$), 3.85 (3H, s, —OCH$_3$), 4.14 (4H, m, —COOCH$_2$, —CH$_2$O), 5.10 (1H, s, C4-H), 5.86 (1H, brs, —NH), 6.91 (4H, m, methoxyphenyl-H), 7.36 (1H, t, Nitrophenyl 5-H), 7.64 (1H, d, Nitrophenyl 6-H), 7.97 (1H, d, Nitrophenyl 4-H), 8.09 (1H, m, Nitrophenyl 2-H).

Preferred Embodiment 16

1,4-dihydro-2,6-dimethyl-4-(3-nitrophenyl)-3,5-pyridine carboxylic acid ethyl ester 2-(N-4-(2-(2-methoxyphenoxy)ethyl)piperazinyl)ethyl ester ($I_{15}$)

Compounds $Ia_4$ 2.29 g (0.005 mol), $Id_2$ 1.19 g (0.005 mol), sodium hydroxide 0.2 g (0.005 mol), and toulene (10 ml) are blended and then refluxed for 2 h, and the pressure reduction and concentration process are performed, and dichloromethane (15 ml) and water (15 ml) are added and blended, and the organic layer is dried by sodium sulfate (anhydrous) and filtered, and the pressure reduction and concentration process are performed, and the remnant silicone tubing chromatography (petroleum ether:ethylacetate, 8:1) is used for separating and obtaining a yellow oil (1.17 g) with a yield rate of 37.6%.

ESI-MS (m/z):609.3 [M+H]$^+$
IR (cm$^{-1}$):3344, 3068, 2939, 1697, 1528, 1504, 1455, 1348, 1252, 1212, 1022, 960, 742, 706
$^1$H-NMR (CDCl$_3$): δ1.23 (3H, t, —COOCH$_2$CH$_3$), 2.35 (6H, s, C$_{2-6}$—CH$_3$), 2.50-2.65 (10H, m, —COOCH$_2$CH$_2$N, piperazidine-H), 2.85 (2H, t, —NCH$_2$CH$_2$O), 3.84 (3H, s, —OCH$_3$), 4.08 (2H, q, —COOCH$_2$CH$_3$), 4.02-4.16 (4H, m, —COOCH$_2$, —CH$_2$O), 5.07 (1H, s, C$_4$—H), 5.81 (1H, brs, —NH), 6.90 (4H, m, methoxyphenyl-H), 7.36 (1H, t, Nitrophenyl 5-H), 7.64 (1H, d, Nitrophenyl 6-H), 7.98 (1H, d, Nitrophenyl 4-H), 8.10 (1H, m, Nitrophenyl 2-H).

Preferred Embodiment 17

1,4-dihydro-2,6-dimethyl-4-(3-nitrophenyl)-3,5-pyridine carboxylic acid ethyl ester 3-(N-4-(2-(2-methoxyphenoxy)ethyl)piperazinyl) propyl ester ($I_{16}$)

With reference to the $I_{15}$ synthesis method, the aforementioned compound is prepared by $Ia_5$ and $Id_2$ with a yield of 32.1%.

ESI-MS (m/z): 623.3 [M+H]$^+$
IR (cm$^{-1}$):3343, 3082, 2945, 2818, 1697, 1528, 1504, 1348, 1307, 1253, 1211, 1121, 1096, 1021, 804, 742, 705, 679
$^1$H-NMR (CDCl$_3$): δ1.22 (3H, t, —COOCH$_2$CH$_3$), 1.77 (2H, m, —COOCH$_2$CH$_2$CH$_2$N), 2.27 (2H, m, —COOCH$_2$CH$_2$CH$_2$N), 2.36 (6H, s, C2,6-CH$_3$), 2.44 (4H, brs, —CH$_2$NCH$_2$), 2.61 (4H, br, —CH$_2$NCH$_2$), 2.86 (2H, t, —NCH$_2$CH$_2$O), 3.84 (3H, s, —OCH$_3$), 4.06-4.16 (6H, m, —COOCH$_2$, —COOCH$_2$, —CH$_2$O), 5.08 (1H, s, C$_4$—H), 5.92 (1H, brs, —NH), 6.90 (4H, m, methoxyphenyl-H), 7.36 (1H, t, Nitrophenyl 5-H), 7.62 (1H, d, Nitrophenyl 6-H), 8.00 (1H, d, Nitrophenyl 4-H), 8.11 (1H, m, Nitrophenyl 2-H).

Preferred Embodiment 18

1,4-dihydro-2,6-dimethyl-4-(3-nitrophenyl)-3,5-pyridine carboxylic acid ethyl ester 2-(N-4-(3-(2-methoxyphenoxy)propyl)piperazinyl)ethyl ester ($I_{17}$)

With reference to the $I_{15}$ synthesis method, the aforementioned compound is prepared by $Ia_4$ and $Id_3$ with a yield of 38.2%.

ESI-MS (m/z):623.4[M+H]$^+$
IR (cm$^{-1}$):2963, 2927, 1689, 1528, 1504, 1348, 1261, 1209, 1020, 801, 706
$^1$H-NMR (CDCl$_3$): δ1.23 (3H, t, —COOCH$_2$CH$_3$), 2.04 (2H, m, —NCH$_2$CH$_2$O), 2.28 (2H, t, —COOCH$_2$CH$_2$N), 2.35 (6H, s, C$_{2-6}$—CH$_3$), 2.50-2.65 (10H, m, —NCH$_2$CH$_2$O, piperazidine-H), 3.85 (3H, s, —OCH$_3$), 4.05-4.18 (4H, m, —COOCH$_2$CH$_3$, —COOCH$_2$, —CH$_2$O), 5.10 (1H, s, C$_4$—H), 5.73 (1H, brs, —NH), 6.89 (4H, m, methoxyphenyl-H), 7.39 (1H, t, Nitrophenyl 5-H), 7.67 (1H, d, Nitrophenyl 6-H), 8.00 (1H, d, Nitrophenyl 4-H), 8.11 (1H, m, Nitrophenyl 2-H).

Preferred Embodiment 19

1,4-dihydro-2,6-dimethyl-4-(3-nitrophenyl)-3,5-pyridine carboxylic acid ethyl ester 3-(N-4-(3-(2-methoxyphenoxy)propyl)piperazinyl)propyl ester ($I_{18}$)

With reference to the $I_{15}$ synthesis method, the aforementioned compound is prepared by $Ia_5$ and $Id_3$, with a yield of 32.7%.

ESI-MS (m/z): 637.4 [M+H]$^+$
IR (cm$^{-1}$):3342, 3069, 2963, 2814, 1698, 1528, 1504, 1348, 1261, 1094, 1020, 800, 742, 703
$^1$H-NMR (CDCl$_3$): δ1.19 (3H, t, —COOCH$_2$CH$_3$), 1.75 (2H, m, —COOCH$_2$CH$_2$CH$_2$N), 1.99 (2H, m, —NCH$_2$CH$_2$CH$_2$O), 2.27 (2H, t, —COOCH$_2$CH$_2$CH$_2$N), 2.32 (6H, s, C$_{2-6}$—CH$_3$), 2.40-2.50 (10H, m, —NCH$_2$CH$_2$CH$_2$O, piperazidine-H), 3.82 (3H, s, —OCH$_3$), 4.05 (6H, m, —COOCH$_2$CH$_3$, —COOCH$_2$, —CH$_2$O), 5.03 (1H, s, C$_4$—H), 5.74 (1H, brs, —NH), 6.89 (4H, m, methoxyphenyl-H), 7.34 (1H, t, Nitrophenyl 5-H), 7.59 (1H, d, Nitrophenyl 6-H), 7.95 (1H, d, Nitrophenyl 4-H), 8.08 (1H, m, Nitrophenyl 2-H).

Preferred Embodiment 20

1,4-dihydro-2,6-dimethyl-4-(3-nitrophenyl)-3,5-pyridinecarboxylic acid methyl ester2-(N-4-(3-(2-methoxyphenoxy)-2-hydroxpropyl)piperazinyl)ethyl ester hydrochloride ($II_1$)

Compounds $Ib_1$ 1.34 g (0.003 mol), IIa 0.54 g (0.003 mol), triethylamine (0.5 ml) and acetonitrile (10 ml) are blended, and reacted at 60□ for 1 hr, and the pressure reduction and concentration process are performed, and dichloromethane (10 ml) is added, blended, and rinsed by water, and the organic layer is dried by sodium sulfate (anhydrous), filtered, and the pressure reduction and concentration process are performed to the filtered liquid, and the remnant silicone tubing chromatography (petroleum ether:ethylacetate, 6:1) is used for separating and obtaining a yellow oil, soluble in ethyl ether (anhydrous) 5 ml, and dry HCl gas at room temperature is passed into the solution until pH=2, and filtered, and dried to obtain a light yellow powder (1.20 g) with a yield rate of 56.3%, and amp of 175-177 □.

ESI-MS (m/z):625.3 [M+H]$^+$
IR (cm$^{-1}$):3349, 3074, 2950, 2837, 2440, 1692, 1527, 1503, 1349, 1254, 1214, 1121, 1099, 1021, 747, 706
$^1$H-NMR (CDCl$_3$): δ2.36 (6H, s, C$_{2-6}$—CH$_3$), 2.45-2.65 (13H, m, 2×-NCH$_2$CH$_2$N, —COOCH$_2$CH$_2$N, —NCH$_2$CH (OH)), 3.65 (3H, s, —COOCH$_3$), 3.85 (3H, s, —OCH$_3$), 4.03 (2H, d, —CH$_2$O), 4.15 (3H, m, —COOCH$_2$CH$_2$N, —OH), 5.10 (1H, s, C$_4$—H), 5.75 (1H, brs, —NH), 6.88-6.96 (4H, m, methoxypheny-H), 7.37 (1H, t, m-Nitrophenyl 5-H), 7.64

(1H, d, m-Nitrophenyl 6-H), 8.00 (1H, d, m-Nitrophenyl 4-H), 8.09 (1H, s, m-Nitrophenyl 2-H).

Preferred Embodiment 21

1,4-dihydro-2,6-dimethyl-4-(3-nitrophenyl)-3,5-pyridinecarboxylic acid methyl ester3-(N-4-(3-(2-methoxyphenoxy)-2-hydroxpropyl)piperazinyl)propyl ester hydrochloride ($II_2$)

With reference to the $I_{11}$ synthesis method, the aforementioned compound is prepared by $Ib_2$ and IIa, with a yield of 52.1%, and a mp of 168~171□.

ESI-MS (m/z):639.2[M+H]$^+$

IR (cm$^{-1}$):3389, 3078, 2950, 2839, 2642, 2439, 1689, 1527, 1503, 1349, 1253, 1216, 1122, 1097, 1019, 957, 747, 706

$^1$H-NMR (CDCl$_3$): δ2.29 (2H, t, —COOCH$_2$CH$_2$CH$_2$N), 2.36 (6H, s, C$_{2-6}$—CH$_3$), 2.58 (12H, m, 2×-NCH$_2$CH$_2$N, —COOCH$_2$CH$_2$CH$_2$N, —NCH$_2$CH(OH)), 3.65 (3H, s, —COOCH$_3$), 3.85 (3H, s, —OCH$_3$), 4.03 (2H, d, —CH$_2$O), 4.10 (3H, m, —COOCH$_2$, —CHOH), 5.08 (1H, s, C$_4$—H), 5.71 (1H, brs, —NH), 6.92 (4H, m, methoxyphenyl-H), 7.37 (1H, t, Nitrophenyl 5-H), 7.64 (1H, d, Nitrophenyl 6-H), 7.99 (1H, d, Nitrophenyl 4-H), 8.10 (1H, s, Nitrophenyl 2-H).

Preferred Embodiment 22

1,4-dihydro-2,6-dimethyl-4-(3-nitrophenyl)-3,5-pyridinecarboxylic acid methyl ester4-(N-4-(3-(2-methoxyphenoxy)-2-hydroxpropyl)piperazinyl)butyl ester hydrochloride ($II_3$)

With reference to the $I_{11}$ synthesis method, the aforementioned compound is prepared by $Ib_3$ and IIa with a yield of 48.7%, and a mp of 142~145□.

ESI-MS (m/z):653.4 [M+H]$^+$

IR (cm$^{-1}$):3341, 3073, 2949, 2836, 2580, 1692, 1527, 1503, 1348, 1253, 1215, 1122, 1097, 1020, 746, 705

$^1$H-NMR (CDCl$_3$): δ1.37 (2H, m, —COOCH$_2$CH$_2$CH$_2$CH$_2$N), 1.55 (2H, m, —COOCH$_2$CH$_2$CH$_2$CH$_2$N), 2.10-2.60 (19H, m, —COOCH$_2$CH$_2$CH$_2$CH$_2$N, C$_{2-6}$—CH$_{3,2}$×-NCH$_2$CH$_2$N, —NCH 2CH(OH)), 3.57 (3H, s, —COOCH$_3$), 3.77 (3H, s, —OCH$_3$), 3.95-4.05 (2H, d, —CH$_2$O), 4.05 (3H, m, —COOCH$_2$, —CHOH), 5.02 (1H, s, C$_4$—H), 5.89 (1H, brs, —NH), 6.80-6.90 (4H, m, methoxypheny-H), 7.29 (1H, t, m-Nitrophenyl 5-H), 7.56 (1H, d, m-Nitrophenyl 6-H), 7.93 (1H, d, m-Nitrophenyl 4-H), 8.02 (1H, s, m-Nitrophenyl 2-H).

While the invention has been described by device of specific embodiments, numerous modifications and variations could be made thereto by those generally skilled in the art without departing from the scope and spirit of the invention set forth in the claims.

What is claimed is:

1. A compound of a general formula (I) or a pharmaceutical salt thereof:

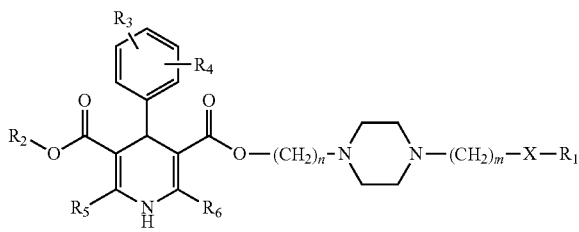

(I)

wherein

R$_1$ represents a substituted or unsubstituted heterocyclic, aromatic ring or aralkyl group, and a substituent is selected from the collection of a C$_1$-C$_4$ alkyl group, a C$_1$-C$_4$ alkoxyl group, a halogen, a cyano-group, a trifluoromethyl group, a trifluoromethoxyl group, a methylthio group, a nitro group, an amino group and a hydroxyl group, R$_2$ represents a C$_1$-C$_8$ alkyl group selected from the collection of an alkyl group having a hydroxyl group or a C$_1$-C$_6$ alkoxyl substituent, R$_3$ and R$_4$ are the same or different, and independently represent hydrogen, halogen, a cyano-group, a trifluoromethyl group, a trifluoromethoxyl group, a methylthio group, a nitro group, an amino group, a C$_1$-C$_4$ an alkyl group, a C$_1$-C$_4$ alkoxyl group, a C$_1$-C$_4$ alkenyl group or a C$_1$-C$_4$ alkinyl group, R$_5$ and R$_6$ are the same or different and represent a C$_1$-C$_4$ alkyl group selected from the collection of an alkyl group having a hydroxyl group and a C$_1$-C$_4$ alkoxyl substituent, X represents O, S or a single bond, m=0-6, n=1-6, and m and n are the same or different.

2. A compound of a general formula (II) or a pharmaceutical salt thereof:

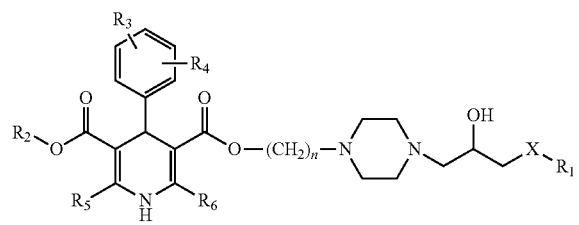

(II)

wherein R$_1$, R$_2$, R$_3$, R$_4$, R$_5$, R$_6$, X, and n are defined the same as claim 1.

3. A compound of a general formula (I) or a pharmaceutical salt thereof:

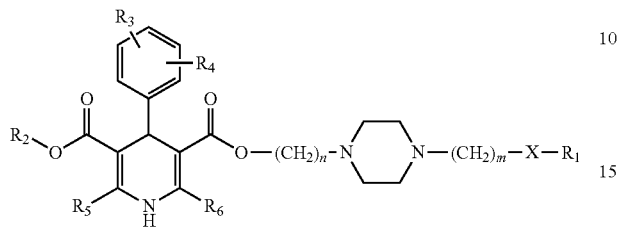

(I)

wherein $R_1$ represents a 2-methooxyphenyl group, a 2,3-dichlorophenyl group, p-nitrophenyl group, p-methylphenyl group or methyl diphenyl group; $R_2$ represents a methyl group, or an ethyl group; $R_3$ represents hydrogen or a 3-nitro group; $R_4$ represents hydrogen or a 3-nitro group; $R_5$ and $R_6$ simultaneously represent methyl groups; X represents O or a single bond; m=0, 1, 2 or 3; and n=2, 3 or 4.

4. The compound of claim 1 or 2 or the pharmaceutical salt thereof, wherein the pharmaceutical salt is an addition salt formed by combining a compound of general formula (I), a compound of general formula (II) and the following acids: sulfuric acid, nitric acid, hydrochloric acid, hydrobromic acid, phosphoric acid, formic acid, acetic acid, maleic acid, citric acid, tartaric acid, lactic acid, benzenesulfonic acid, p-methylbenzenesulfonic acid, pyruvic acid or furamic acid.

5. The compound of claim 1 or 2 or the pharmaceutical salt thereof, wherein the pharmaceutical salt is a monohydrochloride salt or a dihydrochloride salt of the compound of general formulas (I) and (II).

6. A preparation method of a compound or its pharmaceutical salt as recited in claim 1, comprising the step of:

having a substitution reaction between compounds of general formulas Ib and Ic or between compounds of general formulas Ia and Id, and

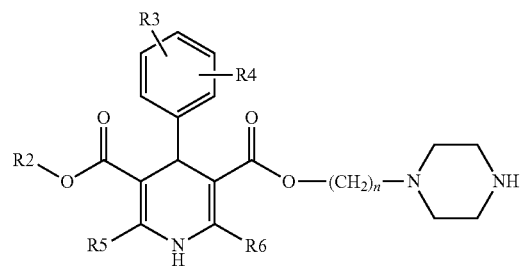

Ib

Ic

Y—(CH₂)ₘ—X—R₁

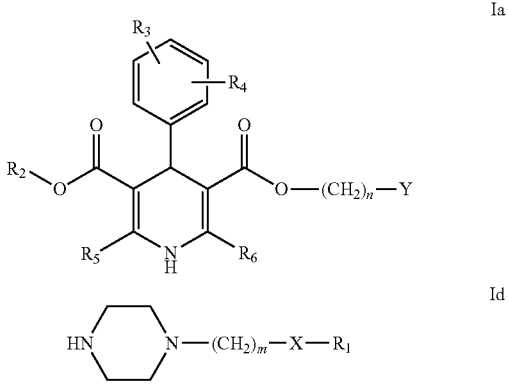

Ia

Id where $R_1, R_2, R_3, R_4, R_5, R_6$, X, m, and n are defined the same as recited in claim 1, and Y represents a halogen atom.

7. The preparation method of claim 6, wherein a compound of general formula Ib has a substitution reaction with a compound of general formula Ic under the catalysis of NaOH; or a compound of general formula Ib has a substitution reaction with a compound of general formula Ic under the catalysis of triethylamine; or a compound of general formula Ib has a substitution reaction with a compound of general formula Ic directly; and a compound of general formula Ia has a substitution reaction with a compound of general formula Id under the catalysis of NaOH; or a compound of general formula Ia has a substitution reaction with a compound of general formula Id under the catalysis of triethylamine; or a compound of general formula Ia has a substitution reaction with a compound of general formula Id directly.

8. A preparation method of a compound or its pharmaceutical salt as recited in claim 2, comprising the step of:

having an addition reaction between a compound of general formula Ib and a compound of general formula IIa under the catalysis of triethylamine, and

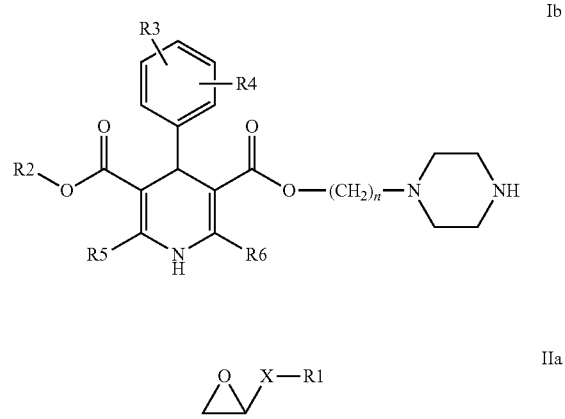

Ib

IIa wherein $R_1, R_2, R_3, R_4, R_5, R_6$, X, and n are defined the same as recited in claim 1.

9. A compound of a general formula (II) or a pharmaceutical salt thereof:

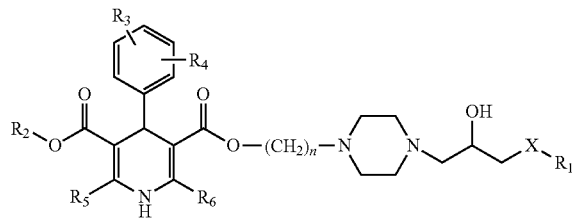

(II)

wherein $R_1$ represents a 2-methooxyphenyl group, a 2,3-dichlorophenyl group, p-nitrophenyl group, p-methylphenyl group or methyl diphenyl group; $R_2$ represents a methyl group, or an ethyl group; $R_3$ represents hydrogen or a 3-nitro group; $R_4$ represents hydrogen or a 3-nitro group; $R_5$ and $R_6$ simultaneously represent methyl groups; X represents O or a single bond; m=0, 1, 2 or 3; and n=2, 3 or 4.

* * * * *